United States Patent
Hirano

(10) Patent No.: US 11,948,341 B2
(45) Date of Patent: Apr. 2, 2024

(54) MEDICAL INFORMATION PROCESSING APPARATUS AND MEDICAL INFORMATION GENERATING APPARATUS

(71) Applicant: CANON MEDICAL SYSTEMS CORPORATION, Otawara (JP)

(72) Inventor: Ryo Hirano, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 308 days.

(21) Appl. No.: 17/388,474

(22) Filed: Jul. 29, 2021

(65) Prior Publication Data
US 2022/0044047 A1    Feb. 10, 2022

(30) Foreign Application Priority Data
Aug. 4, 2020 (JP) ................. 2020-132636

(51) Int. Cl.
G06K 9/00      (2022.01)
G06F 18/22     (2023.01)
(Continued)

(52) U.S. Cl.
CPC ........... *G06V 10/255* (2022.01); *G06F 18/22* (2023.01); *G06T 7/0014* (2013.01); *G06V 10/28* (2022.01); *G06V 10/507* (2022.01); *G16H 30/40* (2018.01); *G16H 50/20* (2018.01); *G06V 10/759* (2022.01); *G06V 2201/03* (2022.01)

(58) Field of Classification Search
None
See application file for complete search history.

(56) References Cited

U.S. PATENT DOCUMENTS

2018/0174284 A1* 6/2018 Semba ............... G06T 7/77
2019/0076027 A1* 3/2019 Nanaumi ........... G06T 5/007

FOREIGN PATENT DOCUMENTS

| JP | 2005-250562 A | 9/2005 |
| JP | 2010-171532 A | 8/2010 |
| JP | 2019-054896 A | 4/2019 |

OTHER PUBLICATIONS

Kayaalti et al., "Liver Fibrosis Staging using CT Image Texture Analysis and Soft Computing", Applied Soft Computing vol. 25 (2014) pp. 399-413.

* cited by examiner

*Primary Examiner* — Wei Wen Yang
(74) *Attorney, Agent, or Firm* — Oblon, McClelland, Maier & Neustadt, L.L.P.

(57) ABSTRACT

A medical information processing apparatus according to an embodiment includes a storage and processing circuitry. The storage is configured to store therein, for each point of a frequency space represented by a plurality of pieces of first frequency component data acquired by applying frequency conversion to data inside regions of interest set to medical images, characteristic data representing a tendency of spectral values that appear at the point. The processing circuitry is configured to acquire second frequency component data by applying frequency conversion to a medical image to be processed, to determine similarity of a spectral value at each point of a frequency space represented by the second frequency component data, with the characteristic data, and to designate a target area in the frequency space represented by the second frequency component data based on the result of the determination.

12 Claims, 12 Drawing Sheets

(51) Int. Cl.
*G06T 7/00* (2017.01)
*G06V 10/20* (2022.01)
*G06V 10/28* (2022.01)
*G06V 10/50* (2022.01)
*G16H 30/40* (2018.01)
*G16H 50/20* (2018.01)
G06V 10/75 (2022.01)

MEDICAL INFORMATION PROCESSING APPARATUS AND MEDICAL INFORMATION GENERATING APPARATUS

CROSS-REFERENCE TO RELATED APPLICATIONS

This application is based upon and claims the benefit of priority from Japanese Patent Application No. 2020-132636, filed on Aug. 4, 2020; the entire contents of which are incorporated herein by reference.

FIELD

Embodiments described herein relate generally to a medical information processing apparatus and a medical information generating apparatus.

BACKGROUND

Having been conventionally practiced is an analysis of a medical image acquired by a modality such as an X-ray CT apparatus, using a diagnosis aiding technology such as a computer-aided diagnosis/detection (CAD). For example, there is a disclosure of a conventional technology for extracting a feature quantity from a piece of data of a region of interest (ROI) set to a medical image, and for determining a medical condition or the name of a disease based on the feature quantity.

The accuracy of the determination made by the technology described above is affected by the data included in the ROI. For example, assuming that to be determined is the condition of a liver tissue, as a target tissue to which the image analysis is to be applied (hereinafter, a target tissue), and that some non-target tissues such as a vessel or extra-hepatic tissue are included in the ROI data, the determination accuracy may become deteriorated due to the effect of the non-target tissues.

DETAILED DESCRIPTION

A medical information processing apparatus according to an embodiment includes a storage and processing circuitry. The storage is configured to store therein, for each point of a frequency space represented by a plurality of pieces of first frequency component data acquired by applying frequency conversion to data inside regions of interest set to medical images, characteristic data representing a tendency of spectral values that appear at the point. The processing circuitry is configured to acquire second frequency component data by applying frequency conversion to a medical image to be processed, to determine similarity of a spectral value at each point of a frequency space represented by the second frequency component data, with the characteristic data, and to designate a target area in the frequency space represented by the second frequency component data, based on the result of the determination.

A medical information processing apparatus and a medical information generating apparatus according to an embodiment will now be explained with reference to some drawings.

Figure 1:
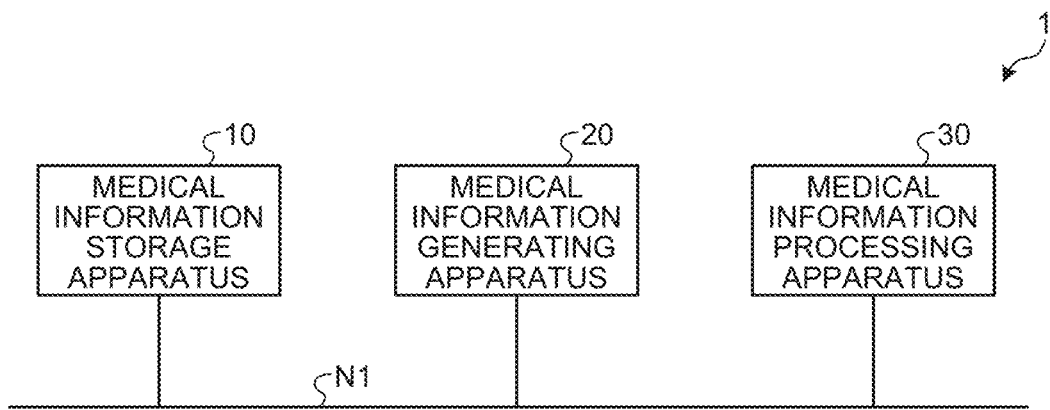
FIG. 1 is a schematic illustrating an exemplary configuration of a medical information processing system according to an embodiment.

FIG. 1 is a schematic illustrating an exemplary configuration of the medical information processing system according to the embodiment. As illustrated in FIG. 1, this medical information processing system 1 includes a medical information storage apparatus 10, a medical information generating apparatus 20, and a medical information processing apparatus 30. The medical information storage apparatus 10, the medical information generating apparatus 20, and the medical information processing apparatus 30 are installed in a medical facility such as a hospital, and are communicatively connected to one another over a network N1, such as an internal network of the hospital.

The medical information storage apparatus 10 includes a database that stores therein medical information of a plurality of subjects. Specifically, the medical information storage apparatus 10 stores therein medical information of each of such subjects in a manner associated with a subject ID for identifying the subject.

The medical information includes at least a medical image. The medical image is an image of the subject acquired using a different type of medical modality, such as an X-ray CT image acquired by an X-ray CT apparatus, an MRI image acquired by an MRI apparatus, an X-ray image acquired by an X-ray apparatus, and a mammography image acquired by a mammography apparatus. Explained in this embodiment is an example in which the medical image is an X-ray CT image acquired by an X-ray CT apparatus, but the embodiment is not limited thereto.

Figure 2:
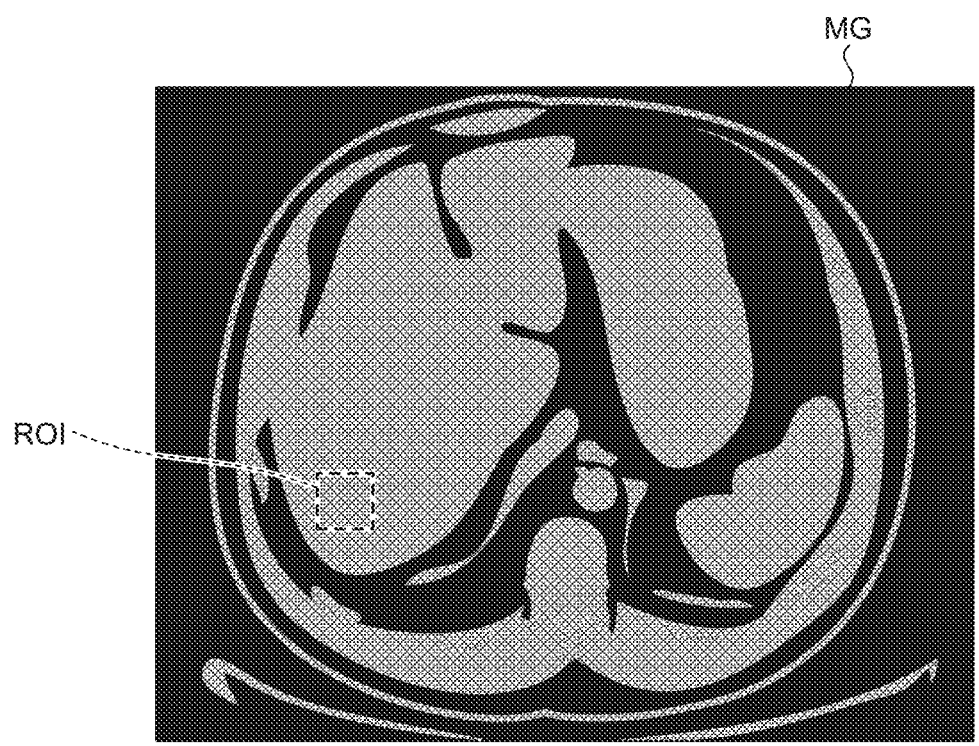
FIG. 2 is a schematic illustrating one example of a medical image according to the embodiment.

FIG. 2 is a schematic illustrating one example of the medical image (X-ray CT image). As illustrated in FIG. 2, a region of interest (hereinafter, also referred to as an ROI) is set to this medical image MG. An ROI is an image area set for the purpose of image analysis.

It is preferable for the ROI set to a medical image in the medical information storage apparatus 10 not to include any non-target tissues other than a target tissue that is the target of the image analysis, or has an extremely small content of the non-target tissues. The "target tissue" herein is a tissue or a region of a living body, the tissue or the region being a main target of the image analysis. The "non-target tissue" means a tissue or a region of a living body other than the target tissue. For example, when the target tissue is a liver tissue, a vessel, an extrahepatic tissue, and the like are non-target tissues.

The medical information storage apparatus 10 stores therein information related to a medical image, information related to a subject, and the like, in a manner associated with a subject ID. For example, the medical information storage apparatus 10 stores therein information indicating a region a medical image of which is captured. The medical information storage apparatus 10 also stores therein, for example, information indicating the result of a diagnosis having been made based on the condition of the ROI included in the medical image, in a manner associated with the medical image. It is preferable for the information indicating a diagnosis result to include a final diagnosis result made by a healthcare professional such as a physician. The diagnosis result herein is a concept including not only the name of a disease but also a binary determination, such as the presence or the absence of a disease, benignancy or malignancy of a disease, or a severity determination represented in a plurality of levels.

The way in which the medical information is stored is not particularly limited, and it is possible to use various forms. For example, the information indicating the region the image of which is captured may be stored in supplemental information that is supplemental to the medical image, or may be stored in an electronic file that is separate from the medical image, e.g., in an electronic medical record. An ROI may be set to (stored in) the medical image itself, or may be stored separately from the medical image, e.g., in an electronic medical record. Furthermore, the information indicating the diagnosis result may also be stored in an electronic file separate from the medical image, e.g., in an electronic medical record.

The medical information generating apparatus 20 performs a process for generating characteristic data, which will be described later, using the medical information of a plurality of subjects stored in the medical information storage apparatus 10. The medical information generating apparatus 20 is implemented as a computer apparatus, such as a personal computer (PC), a workstation, and a server.

The medical information processing apparatus 30 extracts a feature quantity from a medical image to be processed, based on the characteristic data generated by the medical information generating apparatus 20. The medical information processing apparatus 30 performs a diagnosis aiding process, such as determining a disease, based on the extracted feature quantity. The medical information processing apparatus 30 is implemented as a computer apparatus such as a PC, a workstation, and a server.

In the configuration illustrated in FIG. 1, the medical information generating apparatus 20 and the medical information processing apparatus 30 are provided as separate units, but may also be implemented as one apparatus (computer apparatus). Furthermore, the medical information generating apparatus 20 or the medical information processing apparatus 30 may be implemented as a plurality of computer apparatus using cloud computing (cloud).

Configurations of the medical information generating apparatus 20 and the medical information processing apparatus 30 described above will now be explained. To begin with, a configuration of the medical information generating apparatus 20 will be explained with reference to FIG. 3.

Figure 3:
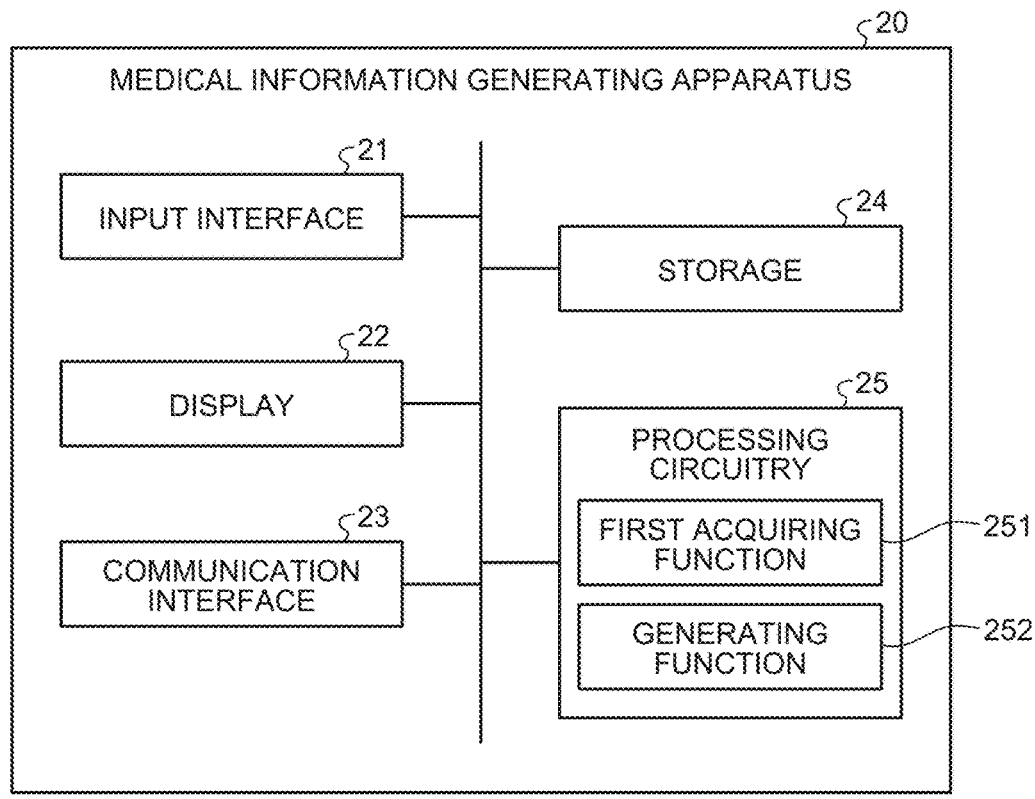
FIG. 3 is a schematic illustrating one example of a configuration of a medical information generating apparatus according to the embodiment.

FIG. 3 is a schematic illustrating one example of a configuration of the medical information generating apparatus 20. As illustrated in FIG. 3, the medical information generating apparatus 20 includes an input interface 21, a display 22, a communication interface 23, a storage 24, and processing circuitry 25. The input interface 21, the display 22, the communication interface 23, the storage 24, and the processing circuitry 25 are connected to one another.

The input interface 21 receives various input operations from an operator, converts the received input operations into electric signals, and outputs the electric signals to the processing circuitry 25. The input interface 21 is implemented as, for example, a mouse, a keyboard, a track ball, a switch, a button, a joystick, a touch pad with which an input operation is made by touching its operation surface, a touch screen in which a display screen and a touch pad are integrated, contactless input circuitry using an optical sensor, and voice input circuitry.

The input interface 21 may be a tablet terminal or the like capable of wirelessly communicating with the main unit of the medical information generating apparatus 20. Furthermore, the input interface 21 is not limited to those having a physical operation component such as a mouse or a keyboard. Another example of the input interface 21 includes electric signal processing circuitry that receives electric signals corresponding to the input operations from an external input device provided separately from the medical information generating apparatus 20, and that outputs the electric signals to the processing circuitry 25.

The display 22 displays various types of information. For example, the display 22 displays the result of processing performed by the processing circuitry 25, under the control of the processing circuitry 25. The display 22 also displays a graphical user interface (GUI) for receiving various instructions, settings, and the like, from an operator via the input interface 21. Examples of the display 22 include a liquid crystal display and a cathode ray tube (CRT) display. The display 22 may be a desktop display, or may be a tablet terminal or the like capable of wirelessly communicating with the main unit of the medical information generating apparatus 20.

The communication interface 23 is an interface for communicating with the various apparatuses connected to the network N1. For example, the processing circuitry 25 can cause the communication interface 23 to exchange various types of data with the medical information storage apparatus 10, and the medical information processing apparatus 30, for example.

The storage 24 is implemented as, for example, a random access memory (RAM), a semiconductor memory device such as a flash memory, a hard disk, or an optical disc. The storage 24 stores therein a computer program for enabling a piece of circuitry included in the medical information generating apparatus 20 to implement its function, for example. The storage 24 also stores therein various types of information acquired from the medical information storage apparatus 10, for example. The storage 24 also stores therein characteristic data (characteristic map), which will be described later, for example.

The processing circuitry 25 controls the overall process performed by the medical information generating apparatus 20. For example, the processing circuitry 25 executes a first acquiring function 251 and a generating function 252, as illustrated in FIG. 3. The first acquiring function 251 is one example of an acquiring unit related to the medical information generating apparatus. The generating function 252 is one example of a generating unit related to the medical information generating apparatus.

For example, the processing functions executed by the first acquiring function 251 and the generating function 252 are stored in the storage 24, in the form of computer-executable programs. The processing circuitry 25 is a processor that implements the functions corresponding to the computer programs by reading the computer programs from the storage 24, and executing the computer programs. In other words, the processing circuitry 25 having read the computer programs comes to have the functions illustrated inside the processing circuitry 25 in FIG. 3.

The first acquiring function 251 performs a process to a group of medical images of a plurality of subjects, the medical images being stored in the medical information storage apparatus 10. In the explanation hereunder, a group of medical images stored in the medical information storage apparatus 10 are sometimes referred to as sample images.

The first acquiring function 251 acquires first conversion data representing a characteristic of ROI data set inside sample images, by converting the ROI data. Specifically, the first acquiring function 251 acquires the first conversion data for each element of the ROI data.

The conversion method is not limited to a particular method as long as the characteristic of the ROI data can be extracted. Specifically, as the conversion method, it is possible to use, for example, frequency conversion such as the Fourier transform with which a spatial frequency characteristic is extracted, or a gray level co-occurrence matrix (GLCM) with which a texture characteristic is extracted.

For example, when the frequency conversion is used as the conversion method, the first acquiring function 251 acquires a power spectrum, as first change data and first frequency component data. The power spectrum herein indicates a power spectral density (hereinafter, referred to as a spectral value) corresponding to each frequency component. When the GLCM is used as the conversion method, the first acquiring function 251 acquires frequencies at which pixel values appear at each pixel, as the first change data. Explained in this embodiment is an example in which the Fourier transform is used as the conversion method.

The first acquiring function 251 acquires a power spectrum of ROI data by applying Fourier transform to the data. Specifically, the first acquiring function 251 acquires a power spectrum by calculating the product of a Fourier coefficient obtained from the Fourier transform with its complex conjugate number.

The algorithm of the Fourier transform is not limited to a particular algorithm, and discrete Fourier transform (DFT), fast Fourier transform (FFT), or the like may be used. With the FFT, it is possible to increase the speed of the power spectrum derivation, compared with when the DFT is used.

Furthermore, when the first acquiring function 251 performs the Fourier transform (e.g., FFT), the first acquiring function 251 may rearrange frequency spaces in such a manner that the low-frequency components appear near the center of the frequency space.

Figure 4:
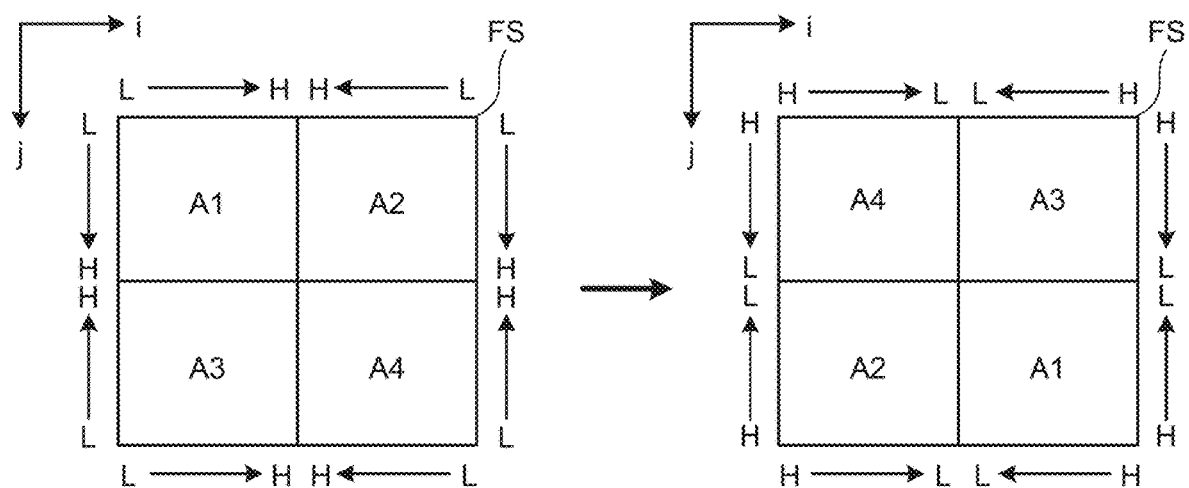
FIG. 4 is a schematic for explaining a frequency space rearrangement operation according to the embodiment.

FIG. 4 is a schematic for explaining a frequency space rearrangement operation. Specifically, as indicated on the left diagram in FIG. 4, in a frequency space FS after the Fourier transform, the low-frequency components (L) are placed at the corners, and high-frequency components (H) are placed near the center.

The first acquiring function 251 divides the frequency space FS into four sub-frequency spaces A1 to A4 by dividing the frequency space FS into two in the direction of a horizontal frequency i, and two in the direction of a vertical frequency j. The first acquiring function 251 then rearranges the sub-frequency spaces A1 to A4 in such a manner that the corners of the sub-frequency spaces A1 to A4 at the four corners of the frequency space FS are brought near the center of the frequency space FS, as indicated in the right diagram in FIG. 4. The right diagram in FIG. 4 is a schematic illustrating the frequency space FS after the rearrangement.

By performing the rearrangement described above, the low-frequency components (L) are placed near the center of the frequency space FS. With such an arrangement, sub-band setting, which will be described later, can be carried out efficiently.

Referring back to FIG. 3, the generating function 252 generates, for each of the elements, characteristic data representing a characteristic of the first conversion data, using pieces of first conversion data acquired from the ROIs of the same type. Specifically, using a group of power spectra acquired from the ROIs of the same type, the generating function 252 generates characteristic data representing statistical characteristics of the power spectrum group, for each of their frequency components.

The "ROIs of the same type" herein means the ROIs set to the same (or similar) regions. For example, the generating function 252 processes a group of power spectra acquired from the ROIs set to the same region (e.g., liver tissue), as a group of power spectra acquired from the ROIs of the same type.

The generating function 252 may also divide the group of power spectra acquired from the ROIs set to the same region, into subgroups, based on the diagnosis results stored in a manner associated with medical images corresponding to the ROIs, as an additional condition for dividing the power spectra into subgroups. For example, the generating function 252 divides a group of power spectra acquired from the ROIs set to the same region, into subgroups of power spectra having the same (or similar) diagnosis results. Explained in this embodiment is an example in which the process is performed by dividing the power spectra into subgroups based on clinical cases. Furthermore, in this embodiment, to simplify the explanation, an example in which the power spectra is divided into subgroups based on two diagnosis results, that is, "negative" and "positive" will be explained.

The generating function 252 according to the embodiment generates, using a group of power spectra acquired from the ROIs of the same type, characteristic data representing statistical characteristics of the group of the power spectra. Specifically, the generating function 252 generates characteristic data representing the appearance frequencies (or appearance probabilities) of spectral values at each of the frequency component (the horizontal frequency i and the vertical frequency j). Hereinafter, the position (point) of a frequency component identified by the horizontal frequency i and the vertical frequency j in the frequency space will be sometimes referred to as a point P(i, j).

Figure 5:
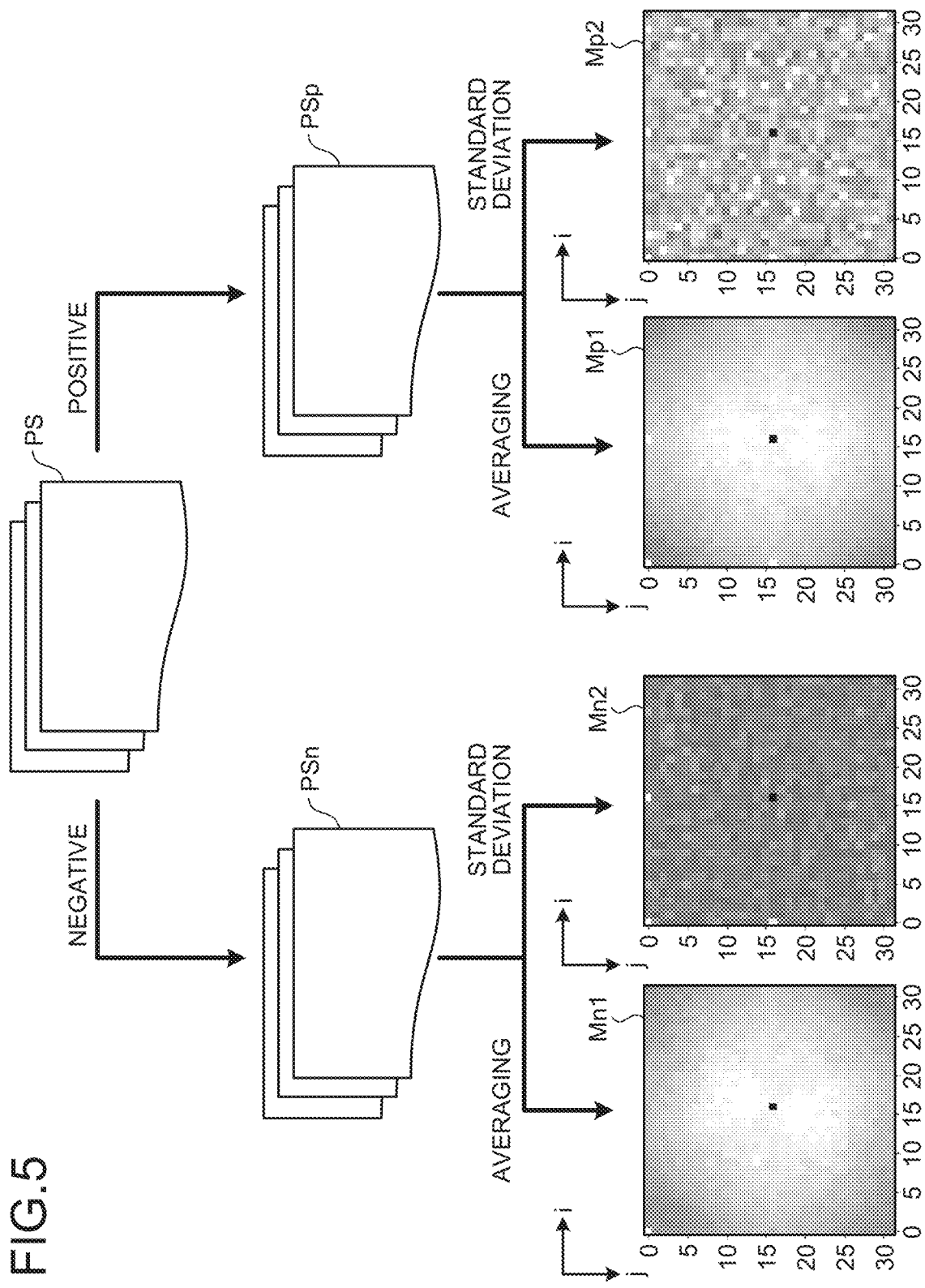
FIG. 5 is a schematic for explaining an exemplary operation performed by a generating function according to the embodiment.

FIG. 5 is a schematic for explaining an exemplary operation performed by the generating function 252. FIG. 5 illustrates an example in which a power spectrum group PS acquired from the ROIs set to the regions of the same type is divided into negative power spectrum group PSn and a positive power spectrum group PSp.

In this example, the generating function 252 generates, for each of the frequency components, a piece of characteristic data representing appearance frequencies of the spectral values, from each of the power spectrum group PSn and the power spectrum group PSp. Specifically, using a predetermined distribution model, the generating function 252 generates a piece of characteristic data for each point P(i, j) of the frequency space represented by a power spectrum group.

For example, assuming that the distribution of the spectral values follows a Gaussian distribution, the appearance frequency (or the appearance probability) $P_{i,j}(x)$ of a spectral value x at each point P(i, j) can be expressed as following Equation (1). Where $\mu$ is an average, and $\sigma^2$ is a variance (where $\sigma$ is a standard deviation).

$$P_{i,j}(x) = \frac{1}{\sqrt{2\pi\sigma_{i,j}^2}} \exp\left(-\frac{(x-\mu_{i,j})^2}{2\sigma_{i,j}^2}\right) \quad (1)$$

The generating function 252 acquires, for each of the power spectrum group PSn and the power spectrum group PSp, a pair of an average $\mu$ and a standard deviation $\sigma$ at each point P(i, j), by substituting the spectral value x at the point P(i, j) into Equation (1). The generating function 252 then generates characteristic data in which the point P(i, j) is mapped to the average $\mu$ and standard deviation $\sigma$ pair acquired for the point P(i, j).

A characteristic map Mn1 in which the average $\mu$ at each point P(i, j) is mapped to the frequency space and a characteristic map Mn2 in which the standard deviation $\sigma$ at each point P(i, j) is mapped to the frequency space are illustrated in FIG. 5, as the characteristic data generated from the negative power spectrum group PSn. In the same manner, a characteristic map Mp1 in which the average $\mu$ at each point P(i, j) is mapped to the frequency space and a characteristic map Mp2 in which the standard deviation $\sigma$ at each point P(i, j) is mapped to the frequency space are illustrated, as the characteristic data generated from the positive power spectrum group PSp.

In these examples, the characteristic maps Mn1, Mp1 represent the values of the average $\mu$ using the darkness of the color, where a lighter color (a color nearer to white) represents a greater average p. The characteristic maps Mn2, Mp2 represent the values of the standard deviation $\sigma$ using the darkness of the color, where a lighter color (a color nearer to white) represents a greater standard deviation $\sigma$. The characteristic data generated by the generating function 252 in the manner described above is statistical representations of the power spectrum group from which the characteristic data is generated, that is, statistical representations of the characteristics of the ROI data of the same type.

The generating function 252 stores the generated characteristic data in the storage 24 or a storage 34 of the medical information processing apparatus 30, in a manner associated with the information related to the ROIs of the same type, from which the characteristic data is generated, or to the medical images, for example. Specifically, the generating function 252 stores the generated characteristic data in a manner associated with information such as the regions where the ROIs are set and the diagnosis results.

In the example described above, the Gaussian distribution has been used as a probability distribution model, but it is also possible to obtain the average $\mu$ and the standard deviation $\sigma$ using another probability distribution model, without limitation to the Gaussian distribution. For example, the generating function 252 may also obtain the average $\mu$ and the standard deviation $\sigma$ assuming that the distribution of the spectral values follows a t distribution or f distribution. As the probability distribution model, it is preferable to use a model that is closer to the actual distribution of the spectral values. By using a probability distribution model that is closer to the actual distribution, effective frequencies, which will be described later, can be determined accurately.

Furthermore, in the example described above, distribution characteristics of the spectral value x at each point P(i, j) is represented using a probability distribution model, but the distribution characteristic may also be represented as a histogram, without limitation to the probability distribution model. In such a case, a histogram can be derived based on the appearance frequencies of the spectral values at each point P(i, j), by using a known technique such as bootstrapping or kernel density estimation (KDE).

Figure 6:
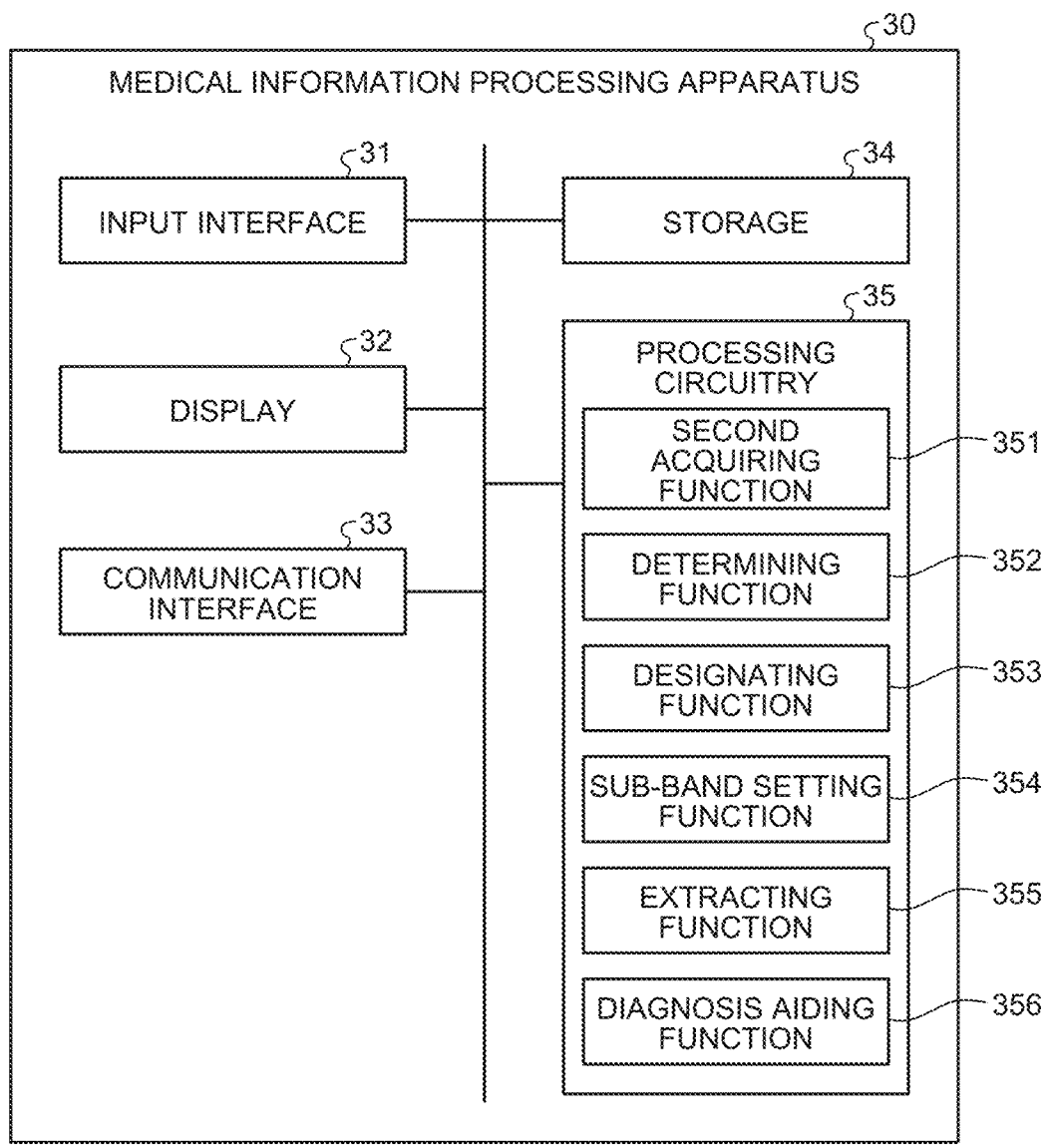
FIG. 6 is a schematic illustrating one example of a configuration of a medical information processing apparatus according to the embodiment.

A configuration of the medical information processing apparatus 30 will now be explained. FIG. 6 is a schematic illustrating one example of a configuration of the medical information processing apparatus 30. As illustrated in FIG. 6, the medical information processing apparatus 30 includes an input interface 31, a display 32, a communication interface 33, a storage 34, and processing circuitry 35. The input interface 31, the display 32, the communication interface 33, the storage 34, and the processing circuitry 35 are connected to one another.

The input interface 31 receives various input operations from an operator, converts the received input operations into electric signals, and outputs the electric signals to the processing circuitry 35. The input interface 31 is implemented as, for example, a mouse, a keyboard, a track ball, a switch, a button, a joystick, a touch pad with which an input operation is made by touching its operation surface, a touch screen in which a display screen and a touch pad are integrated, contactless input circuitry using an optical sensor, and voice input circuitry.

The input interface 31 may also be a tablet terminal or the like capable of wirelessly communicating with the main unit of the medical information processing apparatus 30. Furthermore, the input interface 31 is not limited to those having a physical operation component, such as a mouse or a keyboard. Another example of the input interface 31 includes electric signal processing circuitry that receives electric signals corresponding to the input operations from an external input device provided separately from the medical information processing apparatus 30, and that outputs the electric signals to the processing circuitry 35.

The display 32 displays various types of information. For example, the display 32 displays the result of processing performed by the processing circuitry 35, under the control of the processing circuitry 25. The display 32 also displays a GUI for receiving various instructions, settings, and the like, from an operator via the input interface 31. Examples of the display 32 include a liquid crystal display and a CRT display. The display 32 may be a desktop display, or may be a tablet terminal or the like capable of wirelessly communicating with the main unit of the medical information processing apparatus 30.

The communication interface 33 is an interface for communicating with various apparatuses connected to the network N1. For example, the processing circuitry 35 can cause the communication interface 33 to exchange various types of data with the medical information generating apparatus 20, for example.

The storage 34 is implemented as, for example, a RAM, a semiconductor memory device such as a flash memory, a hard disk, or an optical disc. The storage 34 stores therein a computer program for enabling a piece of circuitry in the medical information processing apparatus 30 to implement its function, for example. The storage 34 also stores therein the characteristic data generated by the medical information generating apparatus 20, for example. In other words, the storage 34 is one example of a storage.

The processing circuitry 35 controls the overall process performed by the medical information processing apparatus 30. For example, the processing circuitry 35 executes a second acquiring function 351, a determining function 352, a designating function 353, a sub-band setting function 354, an extracting function 355, and a diagnosis aiding function 356, as illustrated in FIG. 6. The second acquiring function 351 is one example of the acquiring unit. The determining function 352 is one example of a determining unit. The designating function 353 is one example of a designating unit. The sub-band setting function 354 is one example of a setting unit. The extracting function 355 is one example of an extracting unit. The diagnosis aiding function 356 is one example of a diagnosis aiding unit.

For example, the processing functions executed by the second acquiring function 351, the determining function 352, the designating function 353, the sub-band setting function 354, the extracting function 355, and the diagnosis aiding function 356 are stored in the storage 34, in the form of computer-executable programs. The processing circuitry 35 is a processor that implements the functions corresponding to the computer programs by reading the computer programs from the storage 34, and executing the computer programs. In other words, the processing circuitry 35 having read the computer programs comes to have the functions illustrated inside the processing circuitry 35 in FIG. 6.

The second acquiring function 351 acquires second conversion data by converting the medical image to be processed. Specifically, the second acquiring function 351 acquires second frequency component data (power spectrum) by executing the same frequency conversion as that executed by the first acquiring function 251.

The medical image to be processed means a medical image obtained by capturing an image of the subject for whom a diagnosis is made. The medical image to be processed may be input from a modality (X-ray CT apparatus), or may be acquired from an external apparatus such as the medical information storage apparatus 10, for example.

The medical image to be processed may be the entire medical image obtained by capturing an image of the subject, or ROI data set to the medical image. In the explanation in this embodiment, it is assumed that the medical image to be processed is a piece of ROI data. In the explanation hereunder, an ROI set to the medical image to be processed is sometimes referred to as an ROI to be processed.

It is assumed herein that a healthcare professional such as a physician sets the ROI to the medical image to be processed, but it is also possible for the ROI to be set automatically by a function of the processing circuitry 35, e.g., by the second acquiring function 351, without limitation to a healthcare professional. It is preferable for the size or the shape of the ROI set to the medical image to be processed to be the same as those of the ROI set to the sample images.

The second acquiring function 351 acquires the power spectrum of the ROI data to be processed, by applying Fourier transform to the data. When the second acquiring function 351 performs the Fourier transform, the second acquiring function 351 may also perform the rearrangement of the frequency spaces in such a manner that the low-frequency components appear near the center of the frequency space, in the same manner as that performed by the first acquiring function 251.

The determining function 352 determines the elements having conversion data values similar to the characteristic of the characteristic data, among those of the second conversion data acquired by the second acquiring function 351, based on the characteristic data generated by the medical information generating apparatus 20.

Specifically, the determining function 352 reads the characteristic data to be used in determining the similarity from the storage 24 of the medical information generating apparatus 20. At this time, the determining function 352 may read the entire characteristic data, or a part of the characteristic data. In the latter case, it is preferable for the determining function 352 to read feature data derived from ROIs belonging to the same type that of the ROI to be processed. For example, the determining function 352 reads negative feature data and positive feature data derived from the ROIs set to the same (or similar) region as the ROI to be processed.

The determining function 352 then compares the spectral value at each point P(i, j) of the power spectrum acquired by the second acquiring function 351 with the distribution tendency of a point corresponding thereto specified in the characteristic data, and determines their similarity.

Based on the determination result made by the determining function 352, the designating function 353 designates the frequency components corresponding to a target area in the second conversion data (power spectrum) acquired by the second acquiring function 351, as effective frequencies.

Figure 7:
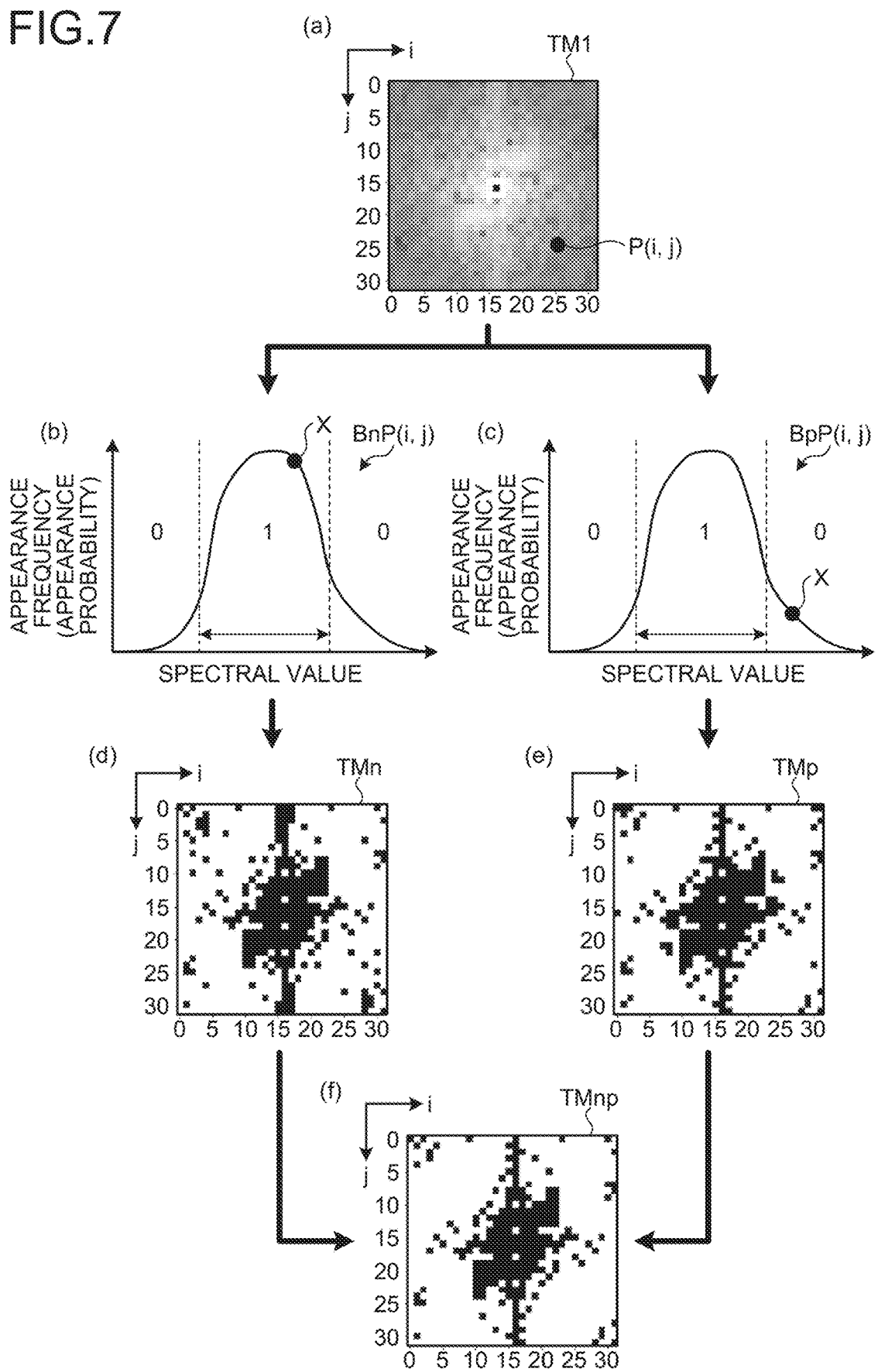
FIG. 7 is a schematic for explaining an exemplary operation performed by a determining function and a designating function according to the embodiment.

An exemplary operation performed by the determining function 352 and the designating function 353 will now be explained with reference to FIG. 7. FIG. 7 is a schematic for explaining an exemplary operation performed by the determining function 352 and the designating function 353.

To begin with, it is assumed that the power spectrum acquired by the second acquiring function 351 is as a target map TM as illustrated in FIG. 7(a). The target map TM is a map in which the spectral value at each point P(i, j) of the power spectrum is represented as a darkness of a color, where a lighter color (closer to white) represents a greater spectral value.

The determining function 352 reads the characteristic data derived from the ROIs of the same type as that of the ROI to be processed, from the storage 24 of the medical information generating apparatus 20. The determining function 352 then determines the similarity between the spectral value at each point P(i, j) of the power spectrum acquired from the second acquiring function 351, based on the read characteristic data.

For example, it is assumed that the negative characteristic data for the point P(i, j) has a distribution BnP(i, j) illustrated in FIG. 7(b), and the positive characteristic data has a distribution BpP(i, j) illustrated in FIG. 7(c). The horizontal axes of the distribution BnP(i, j) and the distribution BpP(i, j) represent spectral values, and the vertical axes represent appearance frequencies (or appearance probabilities). The distribution BnP(i, j) and the distribution BpP(i, j) are derived by applying the average μ and the standard deviation σ at the point P(i, j), retained as the characteristic data, to a statistical model (Gaussian distribution).

In such a case, the determining function 352 identifies the appearance frequency of the spectral value x at the point P(i, j) in the target map TM by plotting the spectral value x to the distribution BnP(i, j) and to the distribution BpP(i, j). The determining function 352 then determines whether there is similarity between the spectral value x at the point P(i, j) in the target map TM with that in the distribution BnP(i, j) and that in the distribution BpP(i, j), as a binary value (1/0), based on the identified appearance frequency. The method for determining the similarity may be set to any method. As an example, the determining function 352 determines that there is similarity when the spectral value x in the target map TM falls within the range of 68% from the average (median) (within the range of average±1σ), as indicated with the arrow in FIG. 7.

For example, the spectral value x in the target map TM falls within the range of 68% in the distribution BnP(i, j). If this is the case, the determining function 352 determines that the spectral value x in the target map TM is similar to the characteristic of the distribution BnP(i, j), that is, to the characteristic of the negative characteristic data. By contrast, the spectral value x in the target map TM does not fall within the range of 68% in the distribution BpP(i, j). In this case, the determining function 352 determines that the spectral value x in the target map TM is not similar to the characteristic of the distribution BpP(i, j), that is, not similar to the characteristic of the positive characteristic data. The determining function 352 determines the presence of similarity for the spectral value x at each point P(i, j), by performing the process described above to all of the points in the target map TM.

A similarity map TMn illustrated in FIG. 7(d) represents the result of the determination of the similarity of each point P(i, j) in the target map TM with the distribution BnP(i, j). In this example, the points determined as being similar are indicated in white, and those determined as being not similar are indicated in black. In the same manner, a similarity map TMp represents the result of the determination of the similarity of each point P(i, j) in the target map TM to the distribution BpP(i, j). The similarity map TMn and the similarity map TMp are one example of map data.

The determining function 352 also generates a synthesized map TMnp illustrated in FIG. 7(f) by taking a logical sum (OR) of the determination results at each point in the similarity map TMn illustrated in FIG. 7(d) and the corresponding point in the similarity map TMp illustrated in FIG. 7(e). For example, establishing a white point having similarity as true (1), and a black point having no similarity as false (0), a point having a true determination result in one of or both of the similarity map TMn and the similarity map TMp is represented as true in the synthesized map TMnp. The synthesized map TMnp is one example of the map data.

The spectral value at a point having true (1) as a determination result in the synthesized map TMnp exhibits similarity to at least one of the negative characteristic data and the positive characteristic data. By contrast, the spectral value at a point having false (0) as a determination result in the synthesized map TMnp exhibits similarity to none of the negative characteristic data and the positive characteristic data.

The designating function 353 then designates the frequency component corresponding to the point where the determination result is true in the synthesized map TMnp, as an effective frequency. When the ROI data from which the characteristic data is generated does not include any non-target tissue or when the ROI data includes little non-target tissues, the spectral value of the frequency component determined to have the similarity to the characteristic data represents a feature of the target tissue. In other words, the designating function 353 designates the area of the frequency components exhibiting the feature of the target tissue, in the frequency space of the power spectrum acquired by the second acquiring function 351, as a target area.

Figure 8:
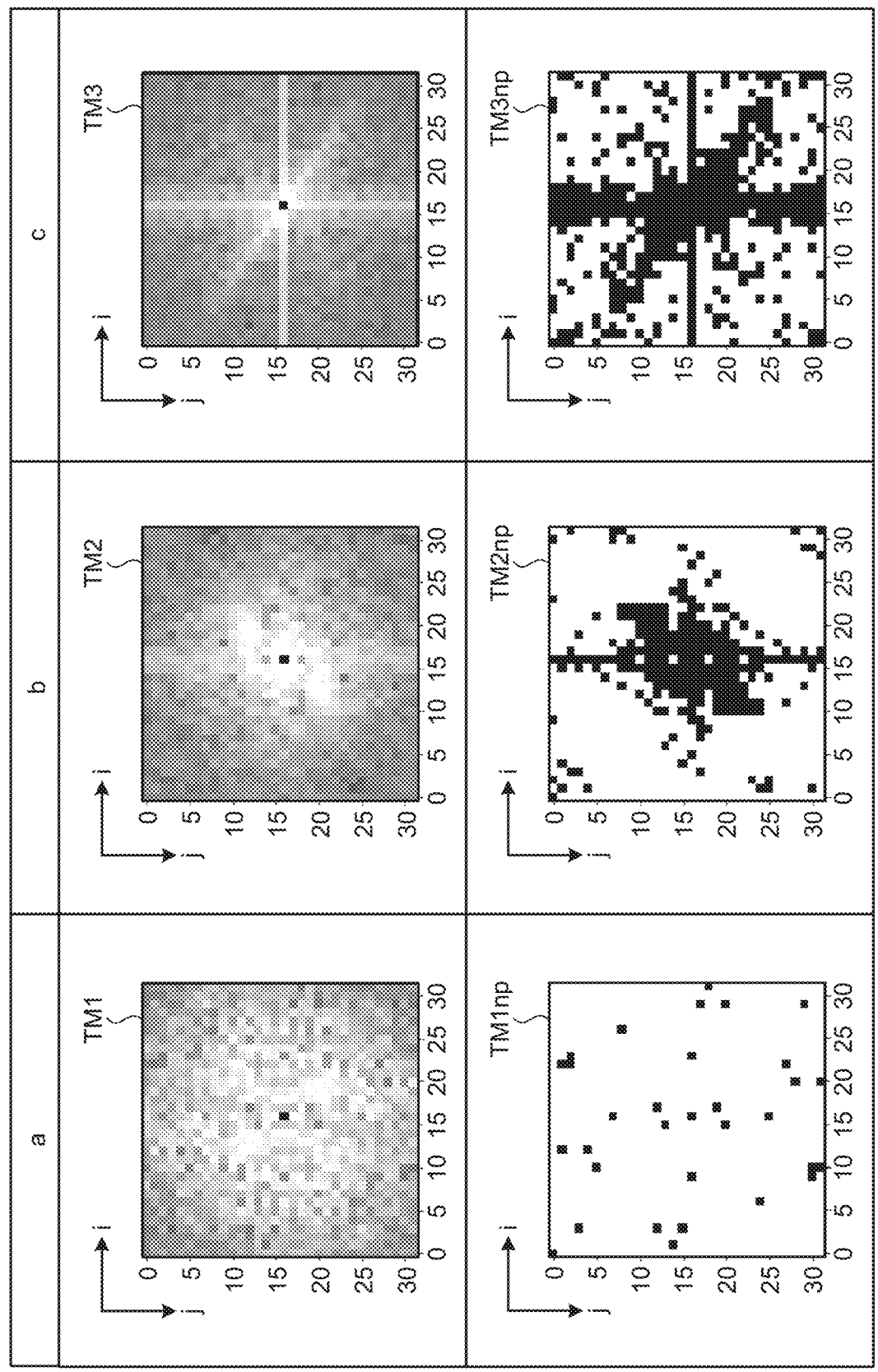
FIG. 8 is a schematic comparatively illustrating pairs of a target map and a synthesized map according to the embodiment.

FIG. 8 is a schematic comparatively illustrating pairs of a target map TM (TM1, TM2, TM3) and a synthesized map TMnp (TM1np, TM2np, TM3np). The target maps TM illustrated in FIG. 8 are acquired from the ROIs set to different regions.

The column (a) in FIG. 8 includes a target map TM1 and a synthesized map TM1np with almost no non-target tissues included in the ROI to be processed. In this example, almost the entire area of the synthesized map TM1np is covered by the white area representing the effective frequency band.

The column (b) in FIG. 8 includes a target map TM2 and a synthesized map TM2np with a small amount of the non-target tissues included in the ROI to be processed. In this example, a small number of black points representing the non-effective frequencies appear in the synthesized map TM2np.

The column (c) in FIG. 8 includes a target map TM3 and a synthesized map TM3np with a large amount of the non-target tissues included in the ROI to be processed. In this example, a large number of black points representing the non-effective frequencies appear in the synthesized map TM3np.

In the manner described above, the ratio between the white points and the black points that appear in the synthesized map TMnp changes depending on the amount of non-target tissues included in the ROI to be processed.

The designating function 353 may be configured to inhibit the ROI to be processed from being used in determining a disease when the ratio occupied by the white points is less than a first threshold in the synthesized map TMnp. At this time, the first threshold may be set to any value, but is preferably set to a value indicating that the ratio of the area occupied by the white points is smaller than that of the area occupied by the black points. For example, when the ratio is as indicated in the synthesized map TM3np illustrated in FIG. 8, the designating function 353 may inhibit the diagnosis aiding function 356 described later from operating, or display a warning message on the display 32, so that the ROI data corresponding to the target map TM3 is not used in determining a disease.

The designating function 353 may also be configured to control to use the entire area of the ROI to be processed in determining a disease when the ratio of the points occupied by white points in the synthesized map TMnp is equal to or more than a second threshold (where the second threshold is greater than the first threshold). At this time, the second threshold may be set to any value, but is preferably set to a value indicating that the ratio of the area occupied by the white points is much greater than that of the area occupied by the black point. For example, when the ratio is as indicated in the synthesized map TM1np illustrated in FIG. 8, the designating function 353 may designate all of the frequency components in the target map TM1 as the effective frequencies.

Referring back to FIG. 6, the sub-band setting function 354 divides the frequency band of the power spectrum acquired by the second acquiring function 351 into a plurality of the frequency ranges (sub-bands). It is assumed herein that the sub-band range into which the frequency band is to be divided is set in advance. Specifically, the sub-band setting function 354 sets one or more sub-bands specified with a predetermined frequency range to the frequency space of the power spectrum.

For example, when the frequency space rearrangement described above has been carried out during the Fourier transform performed by the second acquiring function 351, lower-frequency components have been arranged near the center, going down from the higher-frequency components near the peripheries of frequency space. In such a case, the sub-band setting function 354 can set a plurality of sub-bands having different frequency ranges by setting small areas concentrically from the center of the frequency space, for example. The number of set sub-bands (the number of divisions) is not limited to any particular number, and may be set to any number.

The extracting function 355 extracts the spectral values of the frequency components designated as the effective frequencies as feature quantities, from the power spectrum acquired by the second acquiring function 351, based on the results of the process performed by the designating function 353. The extracting function 355 also extracts, for each of the sub-bands, the feature quantities of the frequency components designated as the effective frequencies, based on the sub-bands set by the sub-band setting function 354.

Figure 9:
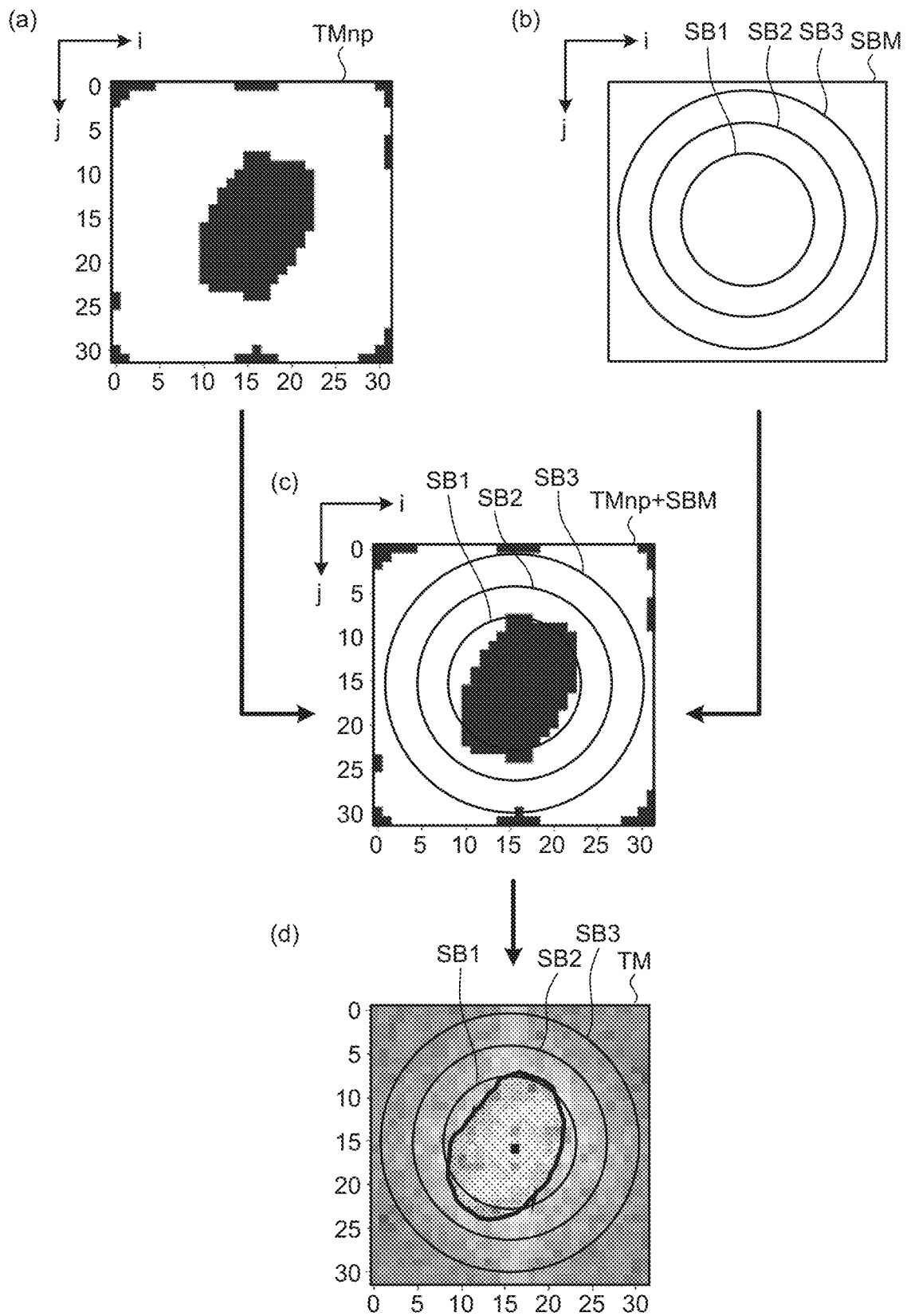
FIG. 9 is a schematic for explaining an exemplary operation performed by a sub-band setting function and an extracting function according to the embodiment.

An exemplary operation performed by the sub-band setting function 354 and the extracting function 355 will now be explained with reference to FIG. 9. FIG. 9 is a schematic for explaining an exemplary operation performed by the sub-band setting function 354 and the extracting function 355.

To begin with, it is assumed that the synthesized map TMnp derived by the designating function 353 is as illustrated in FIG. 9(a). It is also assumed that the sub-bands set to the frequency space by the sub-band setting function 354 is as indicated as a sub-band map SBM illustrated in FIG. 9(b). Illustrated in FIG. 9(b) is an example in which the frequency band of the power spectrum is divided into three sub-bands SB1, SB2, SB3, using the three concentric circles established with their centers at the center of the frequency space.

In such a case, the extracting function 355 extracts the spectral values at the points designated as the effective frequencies, from each of the sub-bands in the frequency space of the power spectrum acquired by the second acquiring function 351, based on the synthesized map TMnp and the sub-band map SBM.

Specifically, the extracting function 355 generates an extraction map TMnp+SBM illustrated in FIG. 9(c) by synthesizing the sub-band map SBM with the synthesized map TMnp. The extracting function 355 then extracts the spectral values at the white points (in the white area) designated as the effective frequencies, from each of the sub-bands in the target map TM illustrated in FIG. 9(d), based on the extraction map TMnp+SBM. The spectral values extracted by the extracting function 355 will serve as feature quantities representing the features of the target tissue included in the ROI to be processed.

Referring back to FIG. 6, the diagnosis aiding function 356 performs a process of determining (estimating) the name of the disease based on the feature quantities extracted by the extracting function 355. Specifically, by inputting some or all of the spectral values extracted from each of the sub-bands, the spectral values being extracted by the extracting function 355, to a classifier, the diagnosis aiding function 356 outputs an estimation result, such as the name of the disease, as diagnosis aiding information. The diagnosis aiding function 356 outputs the diagnosis aiding information to the display 32, for example.

The classifier is not limited to a particular classifier, and any known technology may be used. For example, a support vector machine (SVM) classifier, a logistic regression classifier, a naive bayes classifier, or a decision tree classifier may be used as the classifier.

Furthermore, the diagnosis aiding function 356 may also input information other than the feature quantities extracted by the extracting function 355 to the classifier. For example, the extracting function 355 may input information of the subject pertinent to the medical image being processed (e.g., age, sex, medical history), as the other information.

An exemplary operation performed by the medical information generating apparatus 20 and the medical information processing apparatus 30 described above will now be explained.

Figure 10:
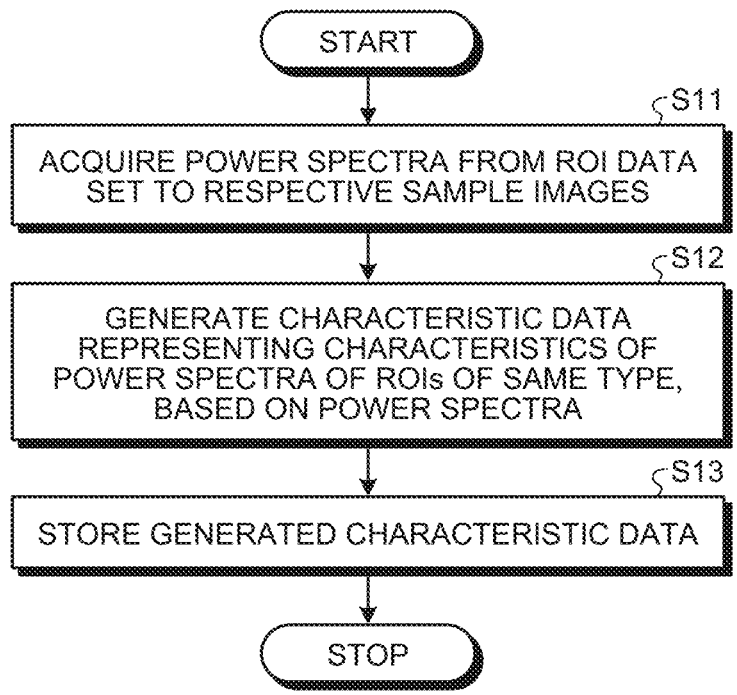
FIG. 10 is a flowchart illustrating one example of a process performed by the medical information generating apparatus according to the embodiment.

FIG. 10 is a flowchart illustrating one example of a process performed by the medical information generating apparatus 20. To begin with, the first acquiring function 251 acquires power spectra from the ROI data set to sample images (Step S11).

The generating function 252 then generates characteristic data representing the characteristics of the power spectra of the ROIs of the same type, based on the power spectra of the ROIs of the same type, among those in the power spectra acquired at Step S11 (Step S12). The generating function 252 may also be configured to generate the characteristic data for each diagnosis result, by further dividing the power spectra acquired from the ROIs of the same type, into those corresponding to the diagnosis results (clinical cases).

The generating function 252 then stores the generated characteristic data in the storage 24 or in the storage 34 of the medical information processing apparatus 30 (Step S13), and ends the process.

Figure 11:
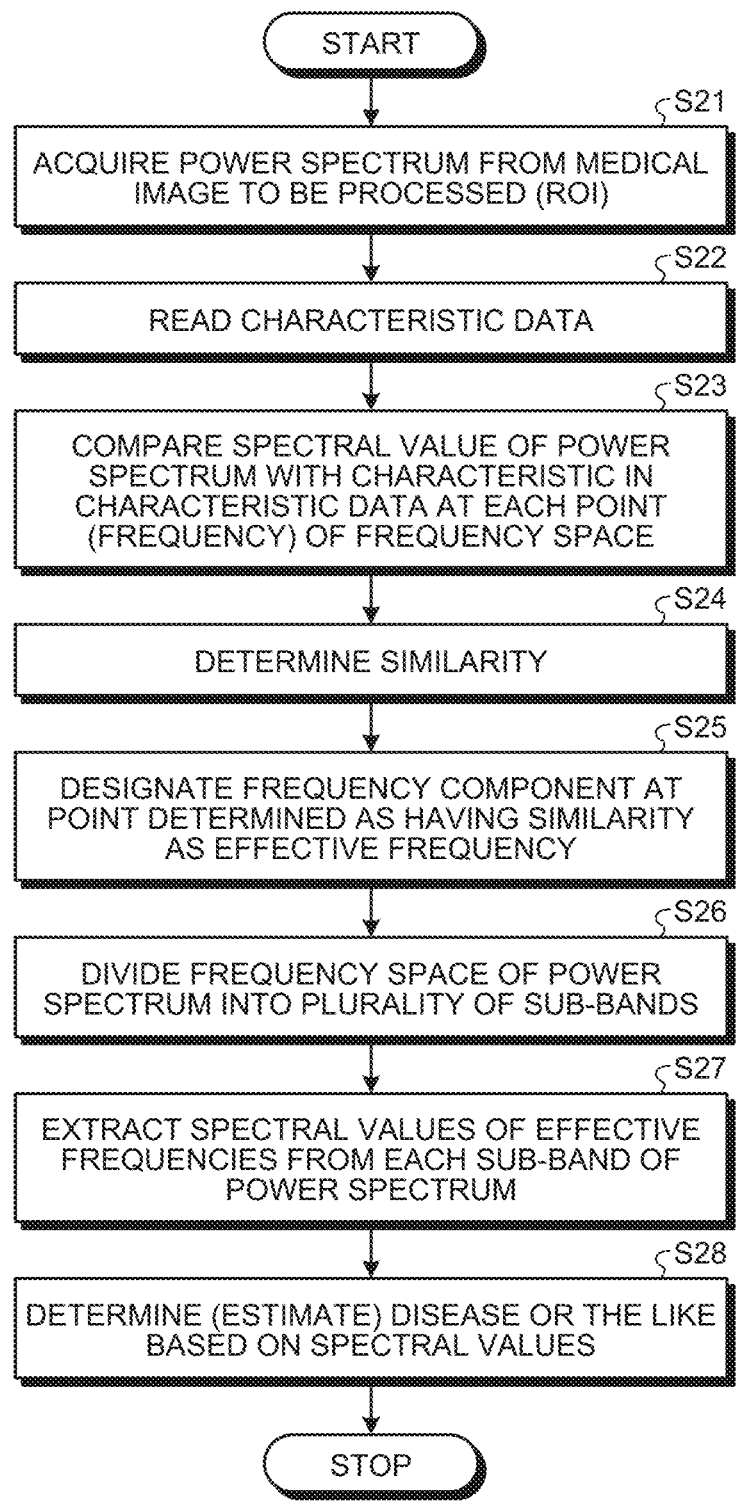
FIG. 11 is a flowchart illustrating one example of a process performed by the medical information processing apparatus according to the embodiment.

FIG. 11 is a flowchart illustrating one example of a process performed by the medical information processing apparatus 30. To begin with, the second acquiring function 351 acquires a power spectrum from a medical image to be processed (ROI) (Step S21). The second acquiring function 351 may perform the frequency space rearrangement described above, when the power spectrum is acquired.

The determining function 352 then reads characteristic data generated from the ROIs of the same type as that of the ROI to be processed, from the medical information generating apparatus 20, for example (Step S22). The determining function 352 then compares the spectral value at each point P(i, j) of the frequency space of the power spectrum acquired at Step S21, with a characteristic corresponding thereto in the characteristic data read at Step S22 (Step S23).

The determining function 352 then determines the similarity between the spectral value at each point P(i, j) of the power spectrum acquired at Step S21, and the characteristic data read at Step S22, based on the result of the comparison at Step S23 (Step S24). The designating function 353 then designates the frequency component at each point P(i, j), the frequency component being determined as having similarity, as an effective frequency, based on the result of the determination performed at Step S24 (Step S25).

The sub-band setting function 354 divides the frequency space of the power spectrum acquired at Step S21 into a plurality of sub-bands (Step S26). The extracting function 355 then extracts the spectral values of the effective frequencies from each of the sub-bands of the power spectrum acquired at Step S21 (Step S27).

The diagnosis aiding function 356 determines (estimates) a disease or the like of the subject, whose image is being processed, based on the spectral values in each of the sub-bands, the spectral values being extracted at Step S27 (Step S28), and ends the process.

As described above, the medical information processing apparatus 30 according to the embodiment acquires a power spectrum by applying frequency conversion to a medical image to be processed; determines similarity between the spectral value at each of the points in the frequency space represented by the power spectrum, with characteristic data representing a tendency of the spectral values appearing at each point P(i, j) of the frequency spaces represented by a plurality of respective power spectra resultant of applying frequency conversion to the data inside the ROIs set to sample images; and designates the target area in the frequency space represented by the power spectrum, having been acquired from the medical image to be processed, based on the result of the determination.

In this manner, with the medical information processing apparatus 30, even when the medical image to be processed (ROI) includes some non-target tissues other than the target tissue, it is possible to designate an area of frequency components corresponding to the target tissue in the frequency space represented by the power spectrum, as a target area, based on the similarity with the characteristic data generated from sample images. Therefore, with the medical information processing apparatus 30, it is possible to extract the data representing a feature of a target tissue efficiently, by extracting spectral values from the designated target area.

As described above, it is also possible to implement the medical information generating apparatus 20 or the medical information processing apparatus 30 described in the embodiment in a manner modified as appropriate, by changing the configuration or the functions provided thereto. Therefore, some of such modifications of the embodiment will now be explained below as other embodiments. In the explanation hereunder, differences from those in the embodiment described above will be mainly explained, and detailed explanations of points that are the same as those already explained above will be omitted. The modification explained below may be implemented individually, or in a manner combined as appropriate.

First Modification

In the configuration according to the embodiment described above, the effective frequencies are designated using the synthesized map TMnp obtained by taking a logical sum of the negative similarity map TMn and the positive similarity map TMp, as it is. In this modification, however, a configuration in which the effective frequencies are designated with the synthesized map TMnp applied with a predetermined process thereto will be explained.

Figure 12:
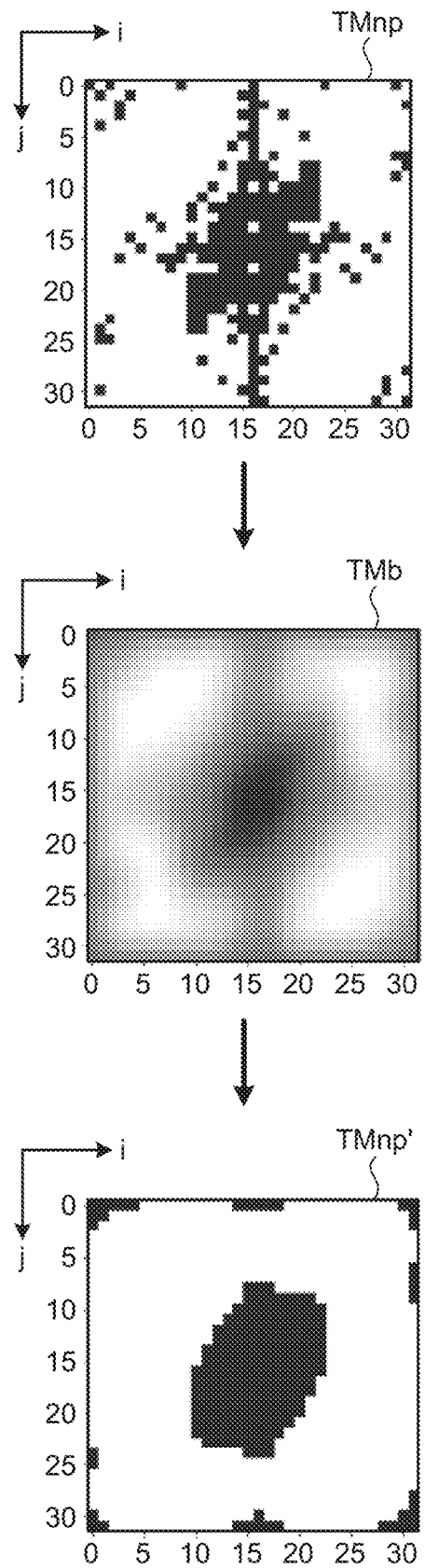
FIG. 12 is a schematic for explaining an exemplary operation performed by a medical information processing apparatus according to a first modification.

FIG. 12 is a schematic for explaining an exemplary operation performed by the medical information processing apparatus 30 according to this modification. To begin with, it is assumed herein that the designating function 353 has derived the synthesized map TMnp illustrated at the top in FIG. 12, by taking a logical sum of the negative similarity map TMn and the positive similarity map TMp, as explained with reference to FIG. 7.

The designating function 353 then applies blurring to the synthesized map TMnp to blur the border between the white points and the black points. As the blurring, a process using various types of filters, such as a Gaussian filter, a moving average filter, or a low-pass filter may be used, for example.

As a result of the blurring, a pixel value represented as a binary value (one bit) of either white (1) or black (0) at each point is converted into multi-value data such as 256-bit data, for example, and an intermediate synthesized map TMb illustrated in the middle in FIG. 12 is obtained.

The designating function 353 then binarizes the pixel value at each point of the intermediate synthesized map TMb again, by performing thresholding to the pixel value. A threshold used in the thresholding may be set to any value, and can be set depending on the resolution of the blurring. As a result of the thresholding, the intermediate synthesized map TMb is turned into a final synthesized map TMnp', illustrated at the bottom in FIG. 12, for example. The designating function 353 then designates the effective frequencies based on the final synthesized map TMnp' by performing the same process as that according to the embodiment described above.

Generally, medical images acquired with various modalities include noise that is dependent on the equipment, the image reconstruction method, and the like. Therefore, the power spectrum obtained from the medical image to be processed also includes such noise. Therefore, due to the effect of the noise included in the power spectrum, for example, the synthesized map TMnp may locally have some points with their pixel values of "1" or "0" reversed.

In such a case, there is a chance for such reversed pixel values, reversed due to the effect of the noise, to be corrected by performing the blurring and the thresholding described above. With the medical information processing apparatus 30 according to a first modification, because the effect of the noise can be reduced, it is possible to improve the accuracy of the determinations of the similarity and the disease further.

Second Modification

Explained in the embodiment above is a configuration in which the binary similarity maps TMn, TMp are derived from the negative distribution BnP(i, j) and the positive distribution BpP(i, j), respectively, but the embodiment is not limited thereto. In this modification, a configuration for deriving continuous-value (multi-value) similarity maps from the negative distribution BnP(i, j) and the positive distribution BpP(i, j) will now be explained.

Figure 13:
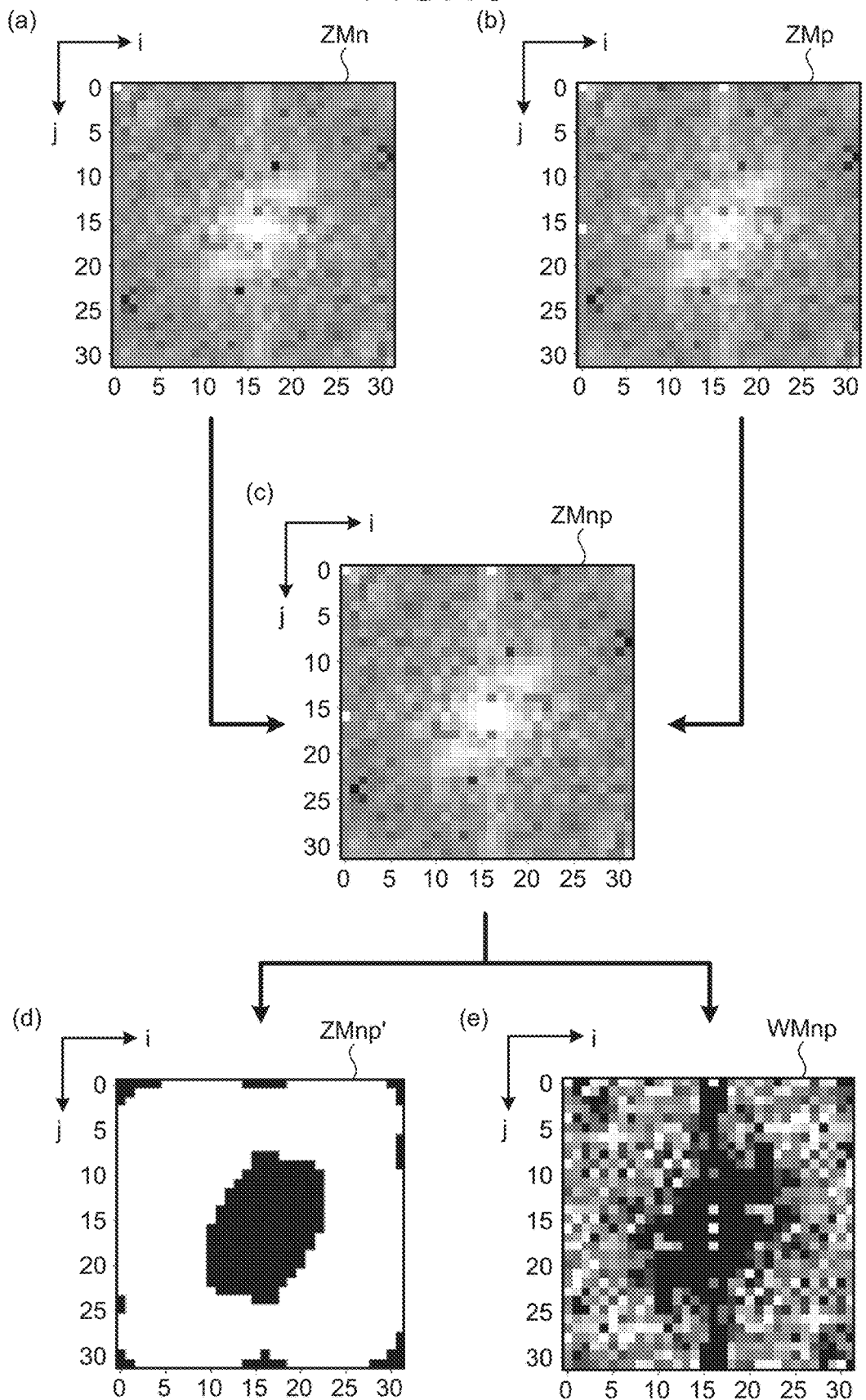
FIG. 13 is a schematic for explaining an exemplary operation performed by a medical information processing apparatus according to a second modification.

FIG. 13 is a schematic for explaining an exemplary operation performed by the medical information processing apparatus 30 according to a second modification. In this modification, it is assumed that the distribution of the spectral values follows a Gaussian distribution.

To begin with, the determining function 352 according to this modification calculates, for the spectral value x at each point P(i, j) of the power spectrum acquired by the second acquiring function 351, Z scores from the negative distribution and the positive distribution of the corresponding point. For example, denoting the Z value calculated from the negative distribution BnP(i, j) as $Z_n(i, j)$, and the Z score calculated from the positive distribution BpP(i, j) as $Zp_{(i,j)}$, $Z_n(i, j)$ and $Zp_{(i,j)}$ can be calculated using Equations (2) and (3) below.

$$Z_n(i, j) = \frac{x - \mu_n}{\sigma_n} \quad (2)$$

$$Z_p(i, j) = \frac{x - \mu_p}{\sigma_p} \quad (3)$$

In Equation (2), $\mu_n$ denotes the average of the negative distribution BnP(i, j) corresponding to the point P(i, j), and $\sigma_n$ denotes the standard deviation of the negative distribution BnP(i, j) corresponding to the point P(i, j). In Equation (3), $\mu_p$ denotes the average of the positive distribution BpP(i, j) corresponding to the point P(i, j), and $\sigma_p$ denotes the standard deviation of the positive distribution BpP(i, j) corresponding to the point P(i, j).

The Z score is a value indicating how many times the standard deviation the spectral value x in the power spectrum pertinent to the point P(i, j) is distanced from the center value of the negative or positive distribution. In other words, the Z score will serve as an index indicating how similar a spectral value in the power spectrum is to the tendency of the negative or the positive distribution. Specifically, inverse of the Z score corresponds to similarity.

The determining function 352 generates a map in which Z scores are mapped to each point P(i, j) of the frequency space (hereinafter, referred to as a Z map), by calculating a negative Z score and a positive Z score for the spectral value x at each point P(i, j) of the power spectrum acquired by the second acquiring function 351.

FIG. 13(a) illustrates a Z map ZMn derived based on the negative feature data, and FIG. 13(b) illustrates a Z map ZMp derived based on the positive feature data. In the Z map ZMn and the Z map ZMp, the Z score at each point P(i, j) is represented as a darkness of the color.

The determining function 352 also generates a synthesized Z map ZMnp illustrated in FIG. 13(c) by synthesizing the Z map ZMn and the Z map ZMp. Specifically, the determining function 352 generates a synthesized Z map ZMnp by calculating the average of $Z_n(i, j)$ at each point P(i, j) in the Z map ZMn and $Zp_{(i, j)}$ at the point corresponding thereto in the Z map ZMp.

The determining function 352 then derives a synthesized Z map ZMnp in which the pixel values are binarized into either "1" represented as white or "0" represented as black, by performing thresholding to the pixel value at each point P(i, j) of the synthesized Z map ZMnp' (FIG. 13(d)). In such a case, the designating function 353 designates the frequency components corresponding to the white points as the effective frequencies, in the same manner as in the embodiment or in the first modification.

The determining function 352 may also generate a weight map specifying weights (weighting coefficients) from the synthesized Z map ZMnp. In such a case, the determining function 352 derives a weight w(i, j) by applying Equation (4) below, for example, to the pixel value at each point P(i, j) of the synthesized Z map ZMnp. $a_{thres}$ denotes a threshold such as "2", and ZMnp(i, j) denotes the pixel value at the point P(i, j).

$$w(i, j) = \begin{cases} \dfrac{a_{thres} - ZMnp(i, j)}{a_{thres}}, & (|ZMnp(i, j)| < a_{thres}) \\ 0, & (|ZMnp(i, j)| \geq a_{thres}) \end{cases} \quad (4)$$

In Equation (4) above, when the absolute value of the pixel value is equal to or more than $a_{thres}$, it is determined that the pixel value exhibits no similarity neither with the negative characteristic data nor with the positive characteristic data, and the weight w(i, j) is set to 0. When the absolute value of the pixel value is smaller than $a_{thres}$, it is determined that the pixel value exhibits similarity to one (or both) of the negative characteristic data and the positive characteristic data, and the weight w(i, j) is set to a value corresponding to the pixel value.

The designating function 353 then derives a weight map WMnp illustrated in FIG. 13(e), by applying Equation (4) above to the pixel value at each point P(i, j) of the synthesized Z map ZMnp, and calculating the weight w(i, j) for the point P(i, j). In the weight map WMnp, the weight w(i, j) at each point is represented as a darkness of the color.

In this case, the designating function 353 designates the frequency components at the points P(i, j) set with the weights w(i, j), as the effective frequencies, based on the weight map WMnp. The extracting function 355 then extracts a value resultant of multiplying the spectral value of each of the frequency components designated as the effective frequencies, among those in the power spectrum acquired by the second acquiring function 351, with the weight w(i, j) at the corresponding point (effective frequency), as a feature quantity.

In the manner described above, the medical information processing apparatus 30 according to this modification extracts the spectral values of the effective frequencies by taking a weight w(i, j) into consideration. In this manner, for example, it is possible to reduce the effect of the non-target tissues given to the determination of a disease, for the effective frequencies largely affected by non-target tissues. Therefore, with the medical information processing apparatus 30 according to this modification, the feature quantity of a target tissue can be extracted efficiently from the medical image to be processed (ROI), and the accuracy of the disease determination can be improved.

Explained in this modification is an example in which the multi-value map is generated using the Z scores, but it is also possible to generate a multi-value map using another index value such as appearance frequencies of the spectral values, or p values, when a distribution model other than the Gaussian distribution is used.

Third Modification

Explained in the embodiment is an example in which the negative similarity map TMn and the positive similarity map TMp are synthesized, but the timing of synthesis is not limited thereto, and the synthesis may take place at the stage of characteristic data. Hereinafter, in this modification, an example in which synthesis takes place at the stage of characteristic data will now be explained.

Figure 14:
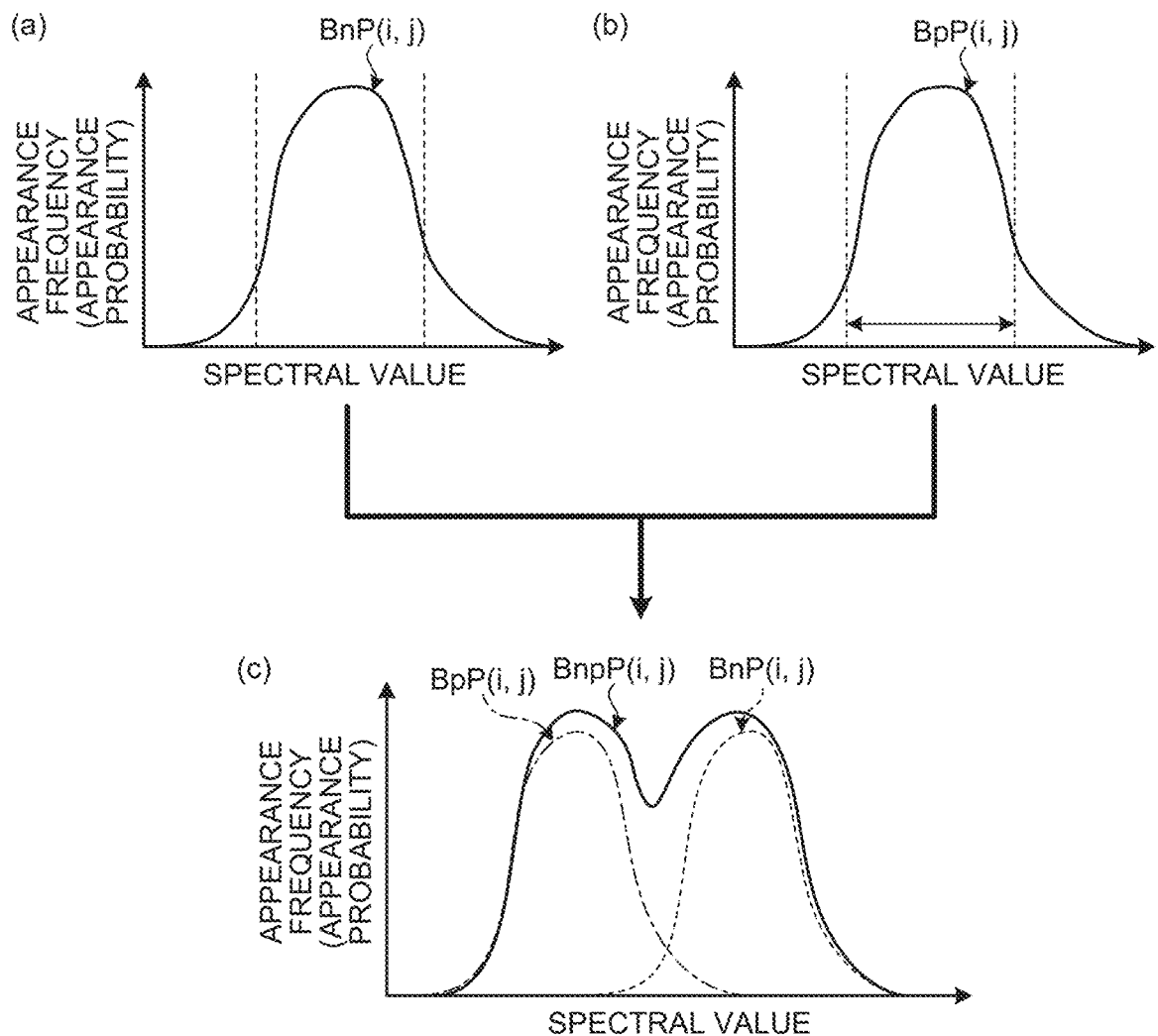
FIG. 14 is a schematic for explaining an exemplary operation performed by a medical information processing apparatus according to a third modification.

FIG. 14 is a schematic for explaining an exemplary operation performed by the medical information processing apparatus 30 according to the third modification. A negative distribution BnP(i, j) illustrated in FIG. 14(a) and a positive distribution BpP(i, j) illustrated in FIG. 14(b) represent the distributions explained with reference to FIGS. 7(b) and 7(c), respectively.

The determining function 352 according to this modification generates a synthesized distribution BnpP(i, j) illustrated in FIG. 14(c), by synthesizing the distribution BnP(i, j) and the distribution BpP(i, j), before determining the similarity. Specifically, the determining function 352 generates a synthesized distribution BnpP(i, j) by adding the appearance frequency of the spectral value in the distribution BnP(i, j) and that of the corresponding spectral value in the distribution BpP(i, j).

The determining function 352 identifies an output frequency by plotting the spectrum at each point P(i, j) and x in the power spectrum acquired by the second acquiring function 351 onto the synthesized distribution BnpP(i, j). The subsequent process is the same as that according to the embodiment described above.

In this manner, the feature quantity of a target tissue can be extracted efficiently from a medical image to be processed (ROI). Therefore, it is possible to achieve the advantageous effects as those achieved in the embodiment described above.

Fourth Modification

Explained in the embodiment is an example in which the characteristic data is generated for the negative and the positive diagnosis results. However, the embodiment is not limited thereto. For example, characteristic data may be generated from a group of power spectra in the ROIs set to the same position and including a mixture of a plurality of clinical cases, and a feature quantity may then be extracted using the characteristic data. In such a case, because the number of steps involved in extracting feature quantities can be reduced, compared with that in the embodiment described above, it is possible to improve the processing efficiency.

Fifth Modification

Explained in the embodiment is an example in which the size or the shape of the ROI set to the medical images is not limited to a particular size or shape, but the processing efficiency can be improved more by setting an ROI considering the following points.

For example, the shape of the ROI may be a rectangle such as a square. When the shape of the ROI is a rectangle, by setting the ROI size to a power of two, e.g., 32 pixels×32 pixels, it is possible to improve the convenience in causing the medical information generating apparatus 20 or the like, which is described above, to apply FFT to the data inside the ROI. Furthermore, even when the size of the ROI is a size other than a power of two, it is also possible to adjust the size to a power of two by padding some appropriate values to the ROI data before performing the FFT.

The shape of the ROI may also be a circle, for example. With such a shape, non-target tissues such as blood vessels can be avoided easily in a process of setting the ROI. When the FFT is to be applied to a circular ROI, it can be achieved by shaping the ROI to a square with a size of a power of two, by filling the area outside the circle with some appropriate data, before performing the FFT.

Furthermore, it is preferable to change the size of the ROI (in pixels) depending on the pixel length of one pixel in the medical image to which the ROI is set, in the real space. Specifically, it is preferable for all of the medical images to have ROIs the sizes of which are substantially the same, after the sizes are converted into those in the real space.

For example, when $l_i$ denotes the length of one pixel in the $i^{th}$ medical image in the real space, and L denotes the length of one side of the ROI in the real space, the number of pixels N in one side of the ROI is expressed as following Equation (5).

$$N = \frac{L}{l_i} \quad (5)$$

By designating the number of pixels in one side of the ROI based on Equation (5), it is possible to make sure that the ROIs in all of the medical images have the same size after their sizes are converted into a size in the real space. In this manner, it is possible to suppress variations in the power spectra that are dependent on the difference in the length of one pixel, due to the way in which the images are captured. In this manner, it is possible to improve the accuracy of the similarity determination, as well as that of the disease determination.

Explained in the embodiment described above (modifications) is an example in which the functional configurations of the medical information generating apparatus 20 and the medical information processing apparatus 30 are implemented by the processing circuitry 25 and the processing circuitry 35, respectively, but the embodiment is not limited thereto. For example, the functional configurations described herein may be achieved with hardware only, or by a combination of hardware and software.

The word "processor" used in the explanation above means circuitry such as a central processing unit (CPU), a graphics processing unit (GPU), an application-specific integrated circuit (ASIC), a programmable logic device (e.g., a simple programmable logic device (SPLD), a complex programmable logic device (CPLD), and a field programmable gate array (FPGA)), for example. When the processor is a CPU, for example, the processor implements a function by reading a computer program stored in a storage, and executing the computer program. When the processor is an ASIC, for example, the function is directly incorporated into the processor circuitry as logic circuitry, instead of a computer program stored in a storage. The processors according to the embodiment are not limited to a configuration in which each of the processors is implemented as a single piece of circuitry, and may also be configured as one processor by combining a plurality of independent pieces of circuitry, and its function may be implemented thereby. Furthermore, it is also possible to integrate a plurality of elements illustrated in the drawings into one processor, and to cause the processor to implement their functions.

The computer program executed by the processor is provided in a manner incorporated in a read-only memory (ROM), a storage, or the like in advance. This computer program may also be provided in a manner recorded in a computer-readable recording medium such as a compact disc (CD)-ROM, a flexible disk (FD), a compact disc recordable (CD-R), or a digital versatile disc (DVD), as a file in a format installable in or executable on these apparatuses. This computer program may also be stored in a computer connected to a network such as the Internet, and provided or distributed by being downloaded over the network. This computer program is configured as modules including the respective functional units described above, for example. As actual hardware, by causing the CPU to read the computer program from a storage such as the ROM, and to execute the computer program, each of the modules is loaded onto the main memory, and generated on the main memory.

With at least one of the embodiments described above, data representing a feature of a target tissue can be extracted efficiently from a medical image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
   a storage configured to store therein, for each point of a first frequency space represented by a plurality of pieces of first frequency component data acquired by applying frequency conversion to data inside first regions of interest that are set to a same corresponding region in a plurality of respective medical images of a plurality of subjects, characteristic data representing a statistical characteristic of spectral values that appear at the point; and processing circuitry configured to acquire second frequency component data by applying the frequency conversion to data inside a second region of interest that is set in a medical image to be processed, compare, for each point of a second frequency space represented by the second frequency component data, a spectral value at the point with a piece of the characteristic data for which the first region of interest is set to a same region as the second region of interest, and determine, with the statistical characteristic represented by the characteristic data based on an appearance frequency at which the spectral value appears, a similarity to the characteristic data, and designate a target area in the second frequency space represented by the second frequency component data, based on a result of the determination.

2. The medical information processing apparatus according to claim 1, wherein the processing circuitry is further configured to determine the similarity based on the characteristic data in which a distribution characteristic of spectral values that appear at a same point is represented by a predetermined probability distribution model or as a histogram.

3. The medical information processing apparatus according to claim 1, wherein the processing circuitry is further configured to integrate a plurality of pieces of the characteristic data, each piece representing, for respective pieces of clinical case, a distribution characteristic of spectral values that appear at a same point, and determine the similarity based on the integrated characteristic data.

4. The medical information processing apparatus according to claim 1, wherein the processing circuitry is further configured to:

generate map data representing a result of the determination of the similarity as a pixel value at each point of the second frequency space, in a manner associated with the point, and designate a target area based on the generated map data.

5. The medical information processing apparatus according to claim 4, wherein the processing circuitry is further configured to:

determine presence of similarity of a spectral value at each point of the second frequency space represented by the second frequency component data, with a plurality of pieces of the characteristic data prepared for a plurality of respective clinical cases, and generate the map data by taking a logical sum of results of determinations of the similarity acquired for the respective clinical cases.

6. The medical information processing apparatus according to claim 4, wherein the processing circuitry is further configured to designate an area occupied by the points determined to have the similarity as the target area.

7. The medical information processing apparatus according to claim 4, wherein the processing circuitry is further configured to execute a process of blurring a border between an area occupied by points determined to have the similarity, and a remaining area, and then to designate the target area based on the pixel values binarized using a predetermined threshold.

8. The medical information processing apparatus according to claim 1, wherein the processing circuitry is further configured to determine the similarity, for each point of the second frequency space represented by the second frequency component data, of a spectral value with the characteristic data, and to designate the target area based on the similarity.

9. The medical information processing apparatus according to claim 1, wherein the processing circuitry is further configured to:

extract spectral values from the target area, and execute a diagnosis aiding process based on the extracted spectral values.

10. The medical information processing apparatus according to claim 9, wherein the processing circuitry is further configured to:

set one or more sub-bands, each of which specifies a predetermined frequency range, to the second frequency space represented by the second frequency component data, and extract spectral values, for each of the sub-bands, from the target area.

11. A medical information processing apparatus, comprising:

a storage configured to store therein, for each point of a first frequency space represented by a plurality of pieces of first frequency component data acquired by applying frequency conversion to data inside first regions of interest that are set to a same corresponding region of a plurality of respective medical images of a plurality of subjects, characteristic data representing a statistical characteristic of data values that appear at the point; and processing circuitry configured to acquire second frequency component data by applying the frequency conversion to data inside a second region of interest that is set in a medical image to be processed, compare, for each point of a second frequency space represented by the second frequency component data, a data value at the point with a piece of the characteristic data for which the first region of interest is set to a same region as the second region of interest, and determine, with the statistical characteristic represented by the characteristic data based on an appearance frequency at which the data value appears, a similarity to the characteristic data, and designate a target area in the second frequency space represented by the second frequency component data, based on a result of the determination.

12. A medical information generating apparatus, comprising:

processing circuitry configured to acquire, for each group of first regions of interest that are set to a same corresponding region of a plurality of respective medical images of a plurality of subjects, a plurality of pieces of first frequency component data by applying frequency conversion to data inside the group of first regions of interest generate, for each point of a frequency space represented by the plurality of pieces of the first frequency component data that are acquired from the group of first regions of interests set to the same region, characteristic data representing a statistical characteristic of spectral values that appear at the point, and store, in a storage, the generated characteristic data associated with information about the group of first regions of interests set to the same region.

* * * * *